(12) United States Patent
Tsujimura et al.

(10) Patent No.: US 8,857,295 B2
(45) Date of Patent: Oct. 14, 2014

(54) SYSTEM FOR PRETREATING SAMPLE

(75) Inventors: Naoto Tsujimura, Hitachinaka (JP); Kazuhiro Noda, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 930 days.

(21) Appl. No.: 12/992,932

(22) PCT Filed: Apr. 14, 2009

(86) PCT No.: PCT/JP2009/001722
§ 371 (c)(1),
(2), (4) Date: Nov. 16, 2010

(87) PCT Pub. No.: WO2009/141957
PCT Pub. Date: Nov. 26, 2009

(65) Prior Publication Data
US 2011/0088517 A1      Apr. 21, 2011

(30) Foreign Application Priority Data

May 22, 2008   (JP) .................................. 2008-134077

(51) Int. Cl.
*B67B 7/00*     (2006.01)
*G01N 35/04*    (2006.01)
*G01N 35/02*    (2006.01)

(52) U.S. Cl.
CPC ........ *G01N 35/04* (2013.01); *G01N 2035/0405* (2013.01); *G01N 35/026* (2013.01)
USPC .................................. 81/3.2; 81/3.44; 29/801

(58) Field of Classification Search
USPC ............ 81/3.2, 3.4, 3.44, 91.3; 269/309, 310; 29/801, 700; 279/2.21–2.24, 35–40, 279/106–109, 110, 123, 152–154
See application file for complete search history.

(56) References Cited

U.S. PATENT DOCUMENTS

| 3,675,916 | A  | * | 7/1972 | Kartasuk et al. ................ 269/69 |
| 6,257,091 | B1 |   | 7/2001 | Cohen et al. |
| 2005/0047966 | A1 |   | 3/2005 | Itoh |
| 2005/0210671 | A1 | * | 9/2005 | Itoh ............................... 29/801 |
| 2009/0142844 | A1 | * | 6/2009 | Le Comte ........................ 436/8 |

FOREIGN PATENT DOCUMENTS

| JP | 5-302927 A | 11/1993 |
| JP | 2000-39438 A | 2/2000 |
| JP | 2003-14770 A | 1/2003 |
| JP | 2005-75395 A | 3/2005 |
| JP | 2005-271991 A | 10/2005 |
| JP | 2007-78363 A | 3/2007 |

* cited by examiner

*Primary Examiner* — Monica Carter
*Assistant Examiner* — Melanie Alexander
(74) *Attorney, Agent, or Firm* — Mattingly & Malur, PC

(57) ABSTRACT

The present invention provides a system for pretreating sample that can unplug a rubber-plugged sample tube and a resin-plugged sample tube in one unplugging unit. The system for pretreating sample includes a sample rack on which a plugged sample tube can be mounted, a conveyor line for conveying the sample rack, and an unplugging unit that has a clamp device for holding the plugged sample tube at the time of unplugging and a plug chuck device for chucking the plug of the plugged sample tube held by the clamp device and unplugging the sample tube. The plug chuck device can unplug both the rubber-plugged and resin-plugged sample tubes. More specifically, the plug chuck device has a combination of an unplugging chuck having a suitable shape for unplugging the rubber-plugged sample tube and another unplugging chuck having a suitable shape for unplugging the resin-plugged sample tube.

11 Claims, 4 Drawing Sheets

FIG. 5A
FIG. 5B
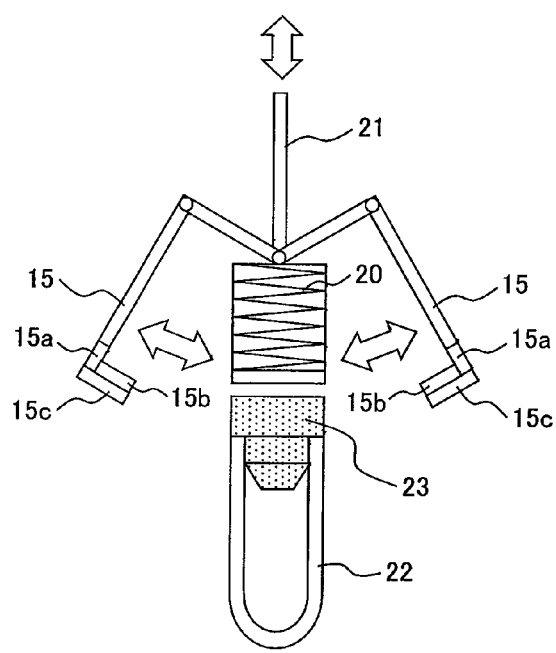
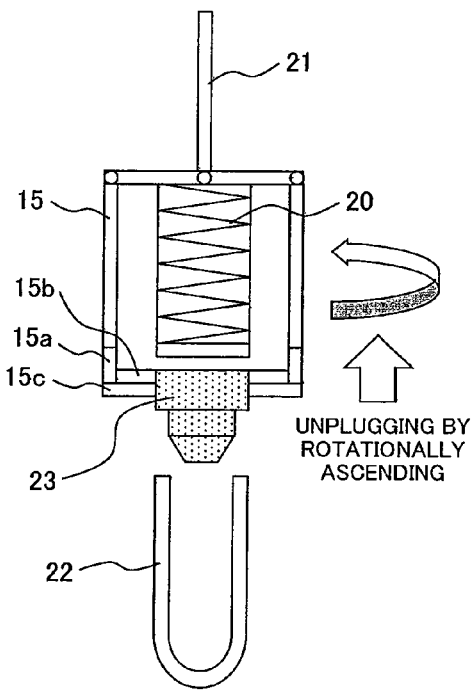
UNPLUGGING BY ROTATIONALLY ASCENDING

SYSTEM FOR PRETREATING SAMPLE

TECHNICAL FIELD

The present invention relates to a system for pretreating sample which automatically pretreat a biological sample (specimen), such as blood or urine, for analysis; and particularly relates to an unplugging technology in a system for pretreating sample having an unplugging unit for unplugging a sample tube.

BACKGROUND ART

A system for pretreating sample conveys a sample rack, on which a sample tube is mounted, to each unit and pretreats a sample. Plugged sample tubes that can be set in a sample rack charge unit generally include a rubber-plugged sample tube, a resin-plugged sample tube, and a seal-type-plugged sample tube. Unplugging process in an unplugging unit must be carried out according to the type of a plug.

A conventional unplugging unit is an exclusive unit conforming to the type of a plug of a plugged sample tube, and basically it cannot treat a mixed group of sample tubes having different types of plugs. Therefore, in a system for pretreating sample having a conventional unplugging unit, a plugged sample tube to be processed must be selected from among the above types. If it is required to use the mixed group of sample tubes at any cost, plural unplugging units should be prepared in an identical system, which is unrealistic from the viewpoint of a space and a cost.

Consequently, when a user introduces a system for pretreating sample, the user needs in advance to select a plugged sample tube to be used from the group including a rubber-plugged sample tube, a resin-plugged sample tube, and a seal-type-plugged sample tube, and it is difficult to comply with user's request to use the mixed group of sample tubes. Further, in an inspection center or the like that collects and processes sample tubes delivered from plural hospitals and others, human workloads have been heavy because of such operation as interchanging samples into a sample tube that can be used in the system for pretreating sample.

PRIOR ART LITERATURE

Patent Literature

Patent Literature 1: JP-A-2003-14770

DISCLOSURE OF THE INVENTION

Problem to be Solved by the Invention

In a conventional technology, in the case of an unplugging unit disclosed in Patent Literature 1 for example, a first unplugging mode switches to a second unplugging mode when an overload sensor detects overload in unplugging operation of the first unplugging mode, and the second unplugging mode switches to the first unplugging mode when the overload sensor detects overload in unplugging operation of the second unplugging mode. The technology is characterized by making it possible to remove a press-in plug and a screw plug by switching the unplugging modes. On this occasion, however, time is wasted during the switching of the unplugging modes by the overload detection, and a decrease in processing capacity is concerned.

Further, in the case of a press-in plug, the state of deformation is different between, for example, a rubber plug and a resin plug at the time of chucking the plug, and hence unplugging may be unsuccessful in an identical unplugging device and an error may occur. This is because, although the deformation of a plug caused by a chuck force during plug chucking is large in the case of a rubber plug and small in the case of a resin plug, the difference by material in the deformation of the plug is not taken into consideration. Consequently, it is desirable that a plug chuck section takes the characteristics of the plug depending on material into consideration. However, nothing is disclosed in Patent Literature 1 about the shape of a plug chuck section or the material of a plug, therefore, there still are problems to be solved for removing both a rubber plug and a resin plug without an error.

An object of the present invention is to provide a system for pretreating sample having an unplugging unit that can unplug a sample tube regardless of whether the material of a plug the sample tube is rubber or resin without a decrease in processing capacity.

Means for Solving the Problem

A system for pretreating sample according to the present invention includes a sample rack on which at least one plugged sample tube containing a collected sample can be mounted; a conveyor line for conveying the sample rack; and an unplugging unit having a clamp device for holding the plugged sample tube at the time of unplugging and a plug chuck device for chucking the plug of the plugged sample tube held by the clamp device and unplugging the sample tube. The plug chuck device can unplug the sample tube having a rubber plug or a resin plug.

More specifically, the system for pretreating sample according to the present invention includes an unplugging chuck having a shape suitable for unplugging a rubber-plugged sample tube and another unplugging chuck having a shape suitable for unplugging a resin-plugged sample tube, both unplugging chucks being combined and arranged in the plug chuck device; and the system for pretreating sample can cope with deformation of each of the plugs at the time of unplugging. Further, in the case where the plug of a sample tube is a screw plug, the sample tube can be unplugged by an operation parameter exclusive to the screw plug instructed by a controller connected to the system for pretreating sample through a communication cable.

Advantages of the Invention

According to the present invention, it is possible to unplug a rubber-plugged sample tube and resin-plugged sample tube with a single unplugging unit in the system for pretreating sample. Therefore, a user can have more choices of a sample tube than ever before, and the system for pretreating sample becomes more flexible.

BRIEF DESCRIPTION OF THE DRAWINGS

FIG. 5A and FIG. 5B are schematic views showing an unplugging operation of an unplugging device according to an embodiment of the present invention.

DETAILED DESCRIPTION OF THE PREFERRED EMBODIMENTS

An embodiment according to the present invention is explained in reference to FIGS. 1 to 5B.

Figure 1:
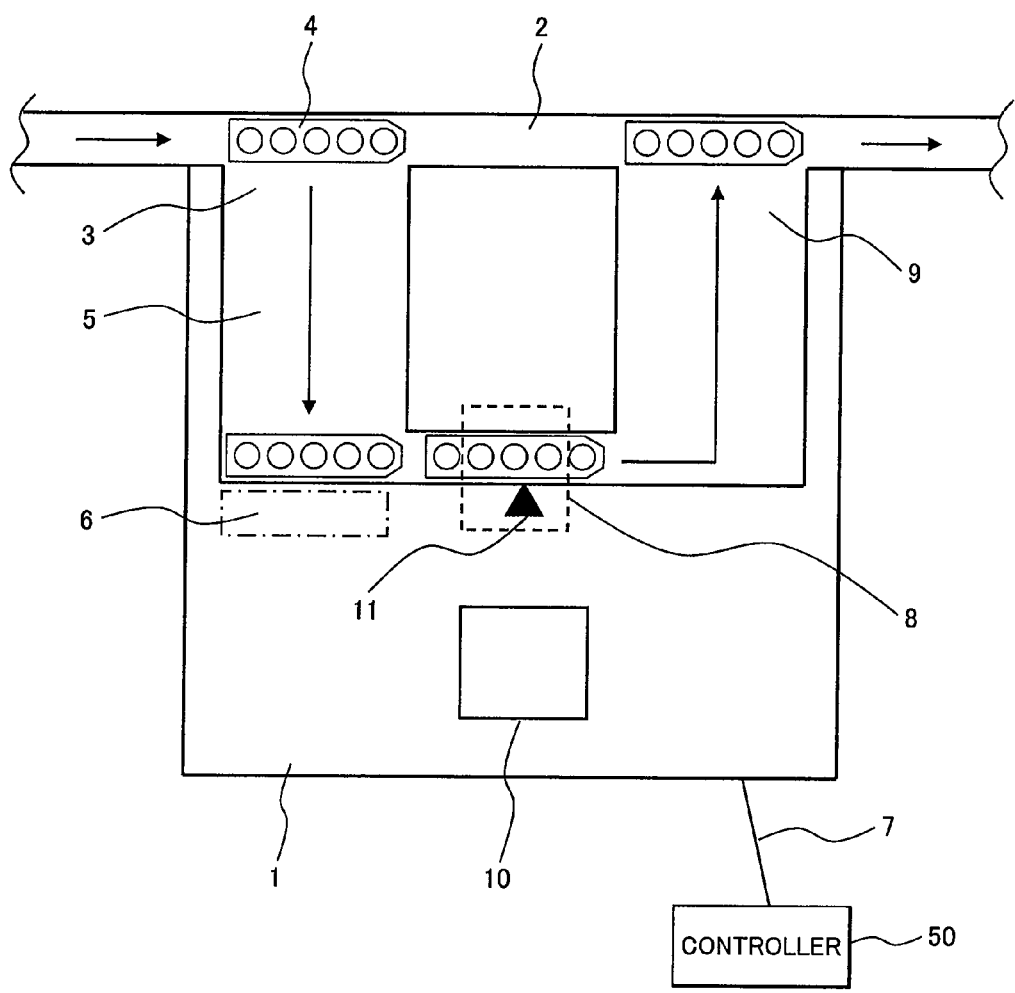
FIG. 1 is a schematic plan view showing an unplugging unit according to an embodiment of the present invention.
Figure 2:
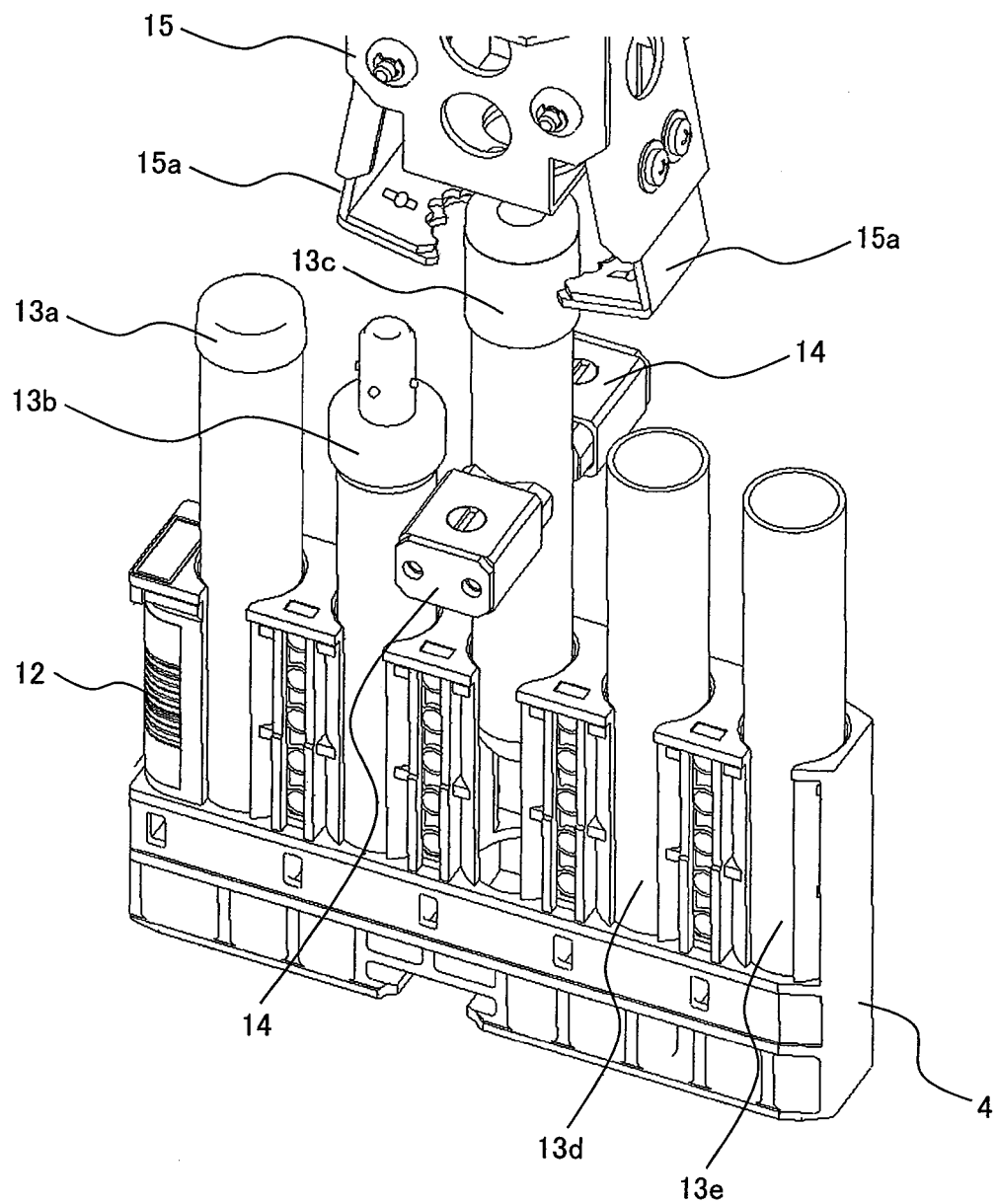
FIG. 2 is a schematic view showing a sample rack, sample tubes, and an unplugging device according to an embodiment of the present invention.

Firstly, an unplugging unit and outline of the processing of the unplugging unit are explained in reference to FIGS. 1 and 2. FIG. 1 is a schematic plan view from above of an unplugging unit in a system for pretreating sample, and FIG. 2 is a schematic view showing a sample rack, sample tubes, and an unplugging device.

An unplugging unit 1 is connected to a conveyor line 2 and brings in a sample rack 4 through a sample rack entrance 3. The sample rack 4 carries sample tubes 13a to 13e as shown in FIG. 2. A rubber press-in plug, a resin screw plug, and a resin press-in plug are attached to the sample tubes 13a, 13b, and 13c, respectively. The sample tubes 13d and 13e are unplugged sample tubes.

The sample rack 4 that has been brought in passes through a buffer 5 and is conveyed to a sample rack identification section 6. The buffer 5 is prepared in order to prevent a stagnation of the sample rack 4 sequentially conveyed from the conveyor line 2.

The sample rack identification section 6 reads an identification number 12 assigned to each of the sample racks 4, transmits the identification number 12 to a controller 50 connected through a communication cable 7, and obtains information on the sample tubes 13a to 13e mounted on the sample rack 4 and instructions on unplugging processing from the controller 50. The information on the sample tubes 13a to 13e includes the heights, the diameters, the presence or absence of the plugs, and the types of the plugs of the sample tubes 13a to 13e. The instructions on unplugging processing include instructions on processing depending on the information on the sample tubes, such as an instruction on whether each of the sample tubes 13a to 13e are to be unplugged or not, and an instruction on operation parameters for the screw plug 13b (parameters on rotary motion necessary at the time of unplugging).

After conveyed to the sample rack identification section 6, the sample rack 4 is conveyed to an unplugging position 8. At the unplugging position 8, an unplugging device is installed above the sample rack 4. When the sample rack 4 is conveyed, the unplugging device descends to carry out unplugging operation in accordance with the information on the sample tubes 13a to 13e and the instructions on unplugging processing obtained from the controller 50, and discards a removed plug to a plug discard position 10. In the case of a sample tube that does not have a plug or that does not require to be unplugged, the unplugging operation is omitted. The unplugging device is described later.

A plug detection sensor 11 for confirming an unplugging state of the sample tube is installed at the unplugging position 8, and when unplugging processing is unsuccessful, the unplugging operation is repeated predetermined times. If the unplugging processing is unsuccessful even when the unplugging operation is repeated predetermined times, an error is generated and reported to the controller 50, and the corresponding sample rack is conveyed from the unplugging unit 1 and stored in an error sample rack storage that is separately installed in a system for pretreating sample.

When the unplugging operation successfully finishes, the sample rack 4 passes through a sample rack exit 9 in the unplugging unit 1, is sent to the conveyor line 2, and is conveyed to a subsequent unit for pretreating sample.

Figure 3:
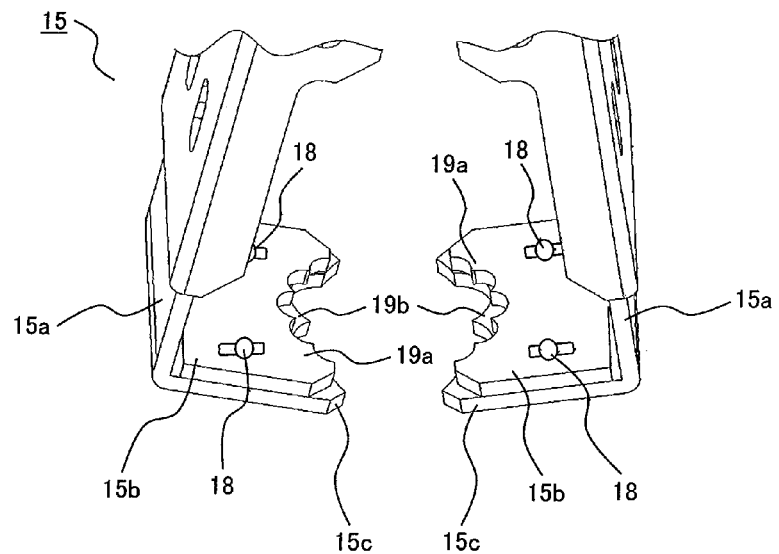
FIG. 3 is a detailed view showing an unplugging chuck according to an embodiment of the present invention.

Successively, an unplugging device and unplugging operation are explained in reference to FIGS. 2, 3, 5A, and 5B. FIG. 2 is a view showing the outline of an unplugging device, a sample rack 4, and sample tubes 13a to 13e as stated earlier. FIG. 3 is a detailed view of an unplugging chuck. FIGS. 5A and 5B are schematic views showing an unplugging operation of an unplugging device.

The plugged sample tubes 13a to 13e mounted on the sample rack 4 are conveyed to the unplugging device installed at the unplugging position 8 through the conveyor line 2 and the buffer 5 (see FIG. 1).

The unplugging device includes a clamp device 14 for holding the plugged sample tubes 13a to 13e one by one and a plug chuck device 15 for unplugging the held plugged sample tube as shown in FIG. 2. The plug chuck device 15 carries out unplugging operation by chucking and upwardly extracting the plug of each of the plugged sample tubes 13a to 13e fixed with the clamp device 14 from opposing two directions.

The outline of unplugging operation using an unplugging device is explained in reference to FIGS. 5A and 5B. Unplugging operation starts when a plugged sample tube 22 is fixed with a clamp device 14 (not shown in FIGS. 5A and 5B). The plug chuck device 15 opens right and left as shown in FIG. 5A when a press section 21 of the unplugging device moves downward and compresses a compression spring 20. Successively, when the compression spring 20 pushes back the press section 21 upward by a repulsive force, the plug chuck device 15 closes and chucks a plug 23 of the plugged sample tube 22 from right and left. The plug chuck device 15, the details of which are described later, includes unplugging chucks 15a having a rubber-plug unplugging chuck 15b and a resin-plug unplugging chuck 15c, and chucks the plug 23 of the sample tube 22 with the unplugging chucks. Then, as shown in FIG. 5B, the plug chuck device 15 rotationally ascends, chucking the plug 23 of the plugged sample tube 22 by the spring force of the compression spring 20. Since the plugged sample tube 22 is fixed with the clamp device 14, only the plug 23 moves and is extracted upward. In this way, the plugged sample tube 22 is unplugged by the unplugging device.

On this occasion, the controller 50 delivers instructions to the plug chuck device 15 on the basis of the information on the sample tubes 13a to 13e obtained at the sample rack identification section 6, and, according to the instructions, the plug chuck device 15 carries out unplugging operation by changing its position in conformity with the height and the outer diameter of each of the sample tubes 13a to 13e.

In the case of the screw plug 13b, unplugging operation of extracting the plug upward is carried out while rotary motion is applied with a torque and a rotating speed different from the case of the press-in plug 13a or 13c, according to the instructions from the controller 50. In this way, motion parameters of the rotary motion at the time of unplugging, such as a torque and a rotating speed, varies with the information on the sample tubes 13a to 13e.

The plug chuck device 15 is explained here. As shown in FIG. 3, the plug chuck device 15 has a pair of elements of the unplugging chucks 15a for unplugging. Each of the unplugging chucks 15a is configured by the combination of the rubber-plug unplugging chuck 15b having a suitable shape for unplugging a rubber-plugged sample tube 13a and the resin-plug unplugging chuck 15c having a suitable shape for a resin-plugged sample tube. The rubber-plug unplugging chuck 15b and the resin-plug unplugging chuck 15c are made of metal, such as stainless steel for example, arranged so that the rubber-plug unplugging chuck 15b is disposed on the upper plane of the resin-plug unplugging chuck 15c, and fixed with screws 18 with each other.

The relative position of the rubber-plug unplugging chuck 15b and the resin-plug unplugging chuck 15c can be changed with the screws 18 in the direction of chucking a plug. That is, the rubber-plug unplugging chuck 15b has screw holes of a long shape in the direction of chucking a plug, and can be used by moving on the resin-plug unplugging chuck 15c and being fixed to a desired position with the screws 18. In this way, by using the unplugging chuck 15a formed by laying the rubber-plug unplugging chuck 15b on the resin-plug unplugging chuck 15c, a sample tube can be unplugged whether the plug is made of rubber or resin.

Further, the rubber-plug unplugging chuck 15b and the resin-plug unplugging chuck 15c respectively have teeth-shaped sections 19a and 19b having plural protrusions (jags) at positions to touch a plug.

Figure 4A:
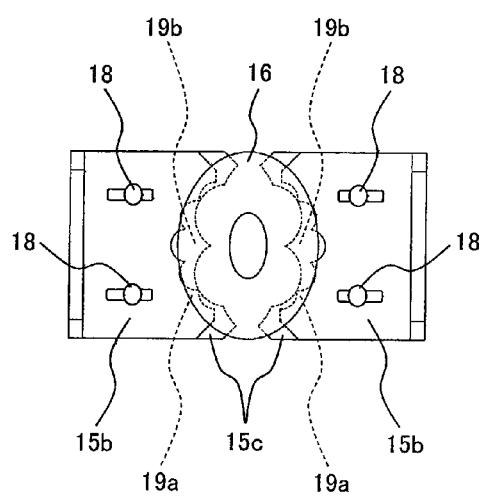
FIG. 4A and FIG. 4B are plan views showing an unplugging chuck at the time of unplugging according to an embodiment of the present invention.
Figure 4B:
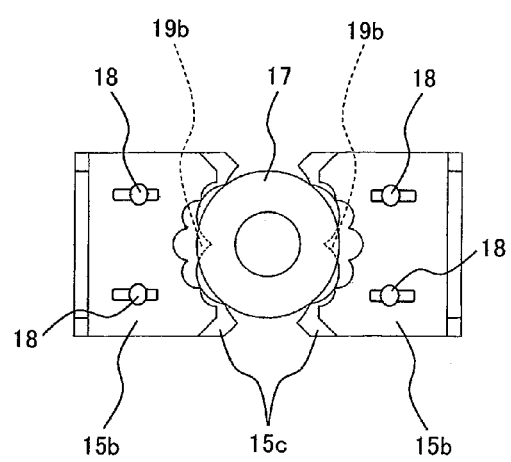

The state of the unplugging chuck 15a at the time of unplugging operation is hereunder explained in reference to FIGS. 4A and 4B.

When the pair of the elements of the unplugging chucks 15a chucks a plug from opposing two directions, the plug deforms by a chuck force. The amount of deformation is different between a rubber plug 16 and a resin plug 17. In general, the amount of deformation is large in the case of the rubber plug 16 (FIG. 4A) and small in the case of the resin plug 17 (FIG. 4B). Further, although friction is large and the unplugging chuck does not slip during unplugging in the case of the rubber plug 16, the friction is small and the unplugging chuck tends to slip in the case of the resin plug 17. Consequently, it is desirable that an unplugging chuck should have a shape in consideration of each characteristic of the rubber plug and the resin plug.

The unplugging chuck 15a according to the present invention is configured by combining the rubber-plug unplugging chuck 15b and the resin-plug unplugging chuck 15c, each of which has a shape in consideration of each characteristic, and hence it is possible to avoid failure in unplugging whether the plug is made of rubber or resin. When unplugging operation is carried out, both the teeth-shaped section 19a of the rubber-plug unplugging chuck 15b and the teeth-shaped section 19b of the resin-plug unplugging chuck 15c press and chuck a plug from opposing two directions and extract the plug upward. The number of teeth (hereunder referred to as "teeth number") of a teeth-shaped section is different between the teeth-shaped section 19a of the rubber-plug unplugging chuck 15b and the teeth-shaped section 19b of the resin-plug unplugging chuck 15c. A larger teeth number is desirable for the rubber plug because the rubber plug has a large amount of deformation by a chuck force and, if the teeth number is small, the whole plug deforms unevenly and unplugging is likely to be unsuccessful, while a smaller teeth number is desirable for the resin plug because, if the teeth number is large, a chuck force disperses and an unplugging chuck slips, likely leading to unsuccessful unplugging. The present invention has a characteristic of using the unplugging chuck 15a that simultaneously satisfies these conflicting requirements to the shape of the unplugging chuck.

The teeth number of the teeth-shaped section 19a of the rubber-plug unplugging chuck 15b is larger than that of the teeth-shaped section 19b of the resin-plug unplugging chuck 15c. The shape is suitable for the deformation of the rubber plug 16, and it is possible to prevent uneven application of a chuck force on a plug due to the deformation and avoid unsuccessful unplugging. Meanwhile, the resin-plug unplugging chuck 15c has a smaller teeth number than the rubber-plug unplugging chuck 15b has so that the resin-plug unplugging chuck 15c can easily transfer a chuck force to the resin plug 17, which has a small amount of deformation, and the chuck force does not disperse and the plug does not slip. More specifically, the teeth number of the rubber-plug unplugging chuck 15b is desirably 5 to 10 and the teeth number of the resin-plug unplugging chuck 15c is desirably 3 or less. The teeth numbers are not limited to those and can be changed as needed.

Further, the resin-plug unplugging chuck 15c is disposed on the lower plane of the rubber-plug unplugging chuck 15b, and the teeth-shaped section 19b, which touches a plug, protrudes into the inside in the direction of chucking the plug beyond the teeth-shaped section 19a of the rubber-plug unplugging chuck 15b. Consequently, when the unplugging chucks 15a chuck a plug, the resin-plug unplugging chuck 15c with a smaller teeth number presses the plug, and then, when the plug deforms and dents, the rubber-plug unplugging chuck 15b with a larger teeth number presses the plug.

In the case where the rubber plug 16 is removed (FIG. 4A), when the resin-plug unplugging chuck 15c with a smaller teeth number firstly presses the plug 16, the plug 16 deforms by a chuck force. On this occasion, although the portion of the plug 16 touching the teeth-shaped section 19b of the resin-plug unplugging chuck 15c is crushed and deforms to dent, the number of concave portions (portions where the chuck force is applied) is smaller because the teeth number is smaller, and hence the portions not touching the teeth-shaped section 1 are pushed out and protrude. This is a state where a chuck force is unevenly applied on the plug 16 and the deformation is also uneven.

Successively, the rubber-plug unplugging chuck 15b presses the plug 16, making the teeth-shaped section 19a with a larger teeth number also apply a chuck force on the protruding portions, and then the whole plug 16 is pressed. Consequently, the state where the chuck force and the deformation are uneven is eliminated and it is possible to hold the chuck force with the whole plug 16 and carry out unplugging operation without failure.

On the other hand, in the case where the resin plug 17 is removed (FIG. 4B), since the deformation of the plug 17 by a chuck force is small, only the resin-plug unplugging chuck 15c disposed on the lower plane of the rubber-plug unplugging chuck 15b presses the plug 17, and the rubber-plug unplugging chuck 15b does not press the plug 17. The resin-plug unplugging chuck 15c, having the teeth-shaped section 19b with a smaller teeth number, presses the plug 17 without dispersing the chuck force and causing slippage and can carry out unplugging operation without failure.

As stated earlier, the positional relationship for the combination of the rubber-plug unplugging chuck 15b and the resin-plug unplugging chuck 15c is set adjustably in the direction of chucking a plug. With this configuration, it is possible to cope flexibly with the differences in outer diameter, material, and hardness of a plug and remove the plug without failure whatever the plug might be.

In the above embodiment, a case have been explained where the resin-plug unplugging chuck 15c is disposed on the lower plane of the rubber-plug unplugging chuck 15b as shown in FIG. 3. With regard to the positioning of the rubber-plug unplugging chuck 15b and the resin-plug unplugging chuck 15c, it is also possible to dispose the rubber-plug unplugging chuck 15b on the lower plane of the resin-plug unplugging chuck 15c in accordance with the shape of a plug. Even in the case of such arrangement, by making the positional relationship variable for the combination of the rubber-plug unplugging chuck 15b and the resin-plug unplugging chuck 15c, it is possible to prevent dispersion of a chuck force and deformation of a plug due to the chuck force, enabling the plug to be removed without failure whatever the plug might be.

As stated earlier, with regard to the material of a plug, it is effective to use the rubber-plug unplugging chuck 15b, which has a larger teeth number to prevent deformation of a plug due to a chuck force, for an elastic material including rubber; and it is effective to use the resin-plug unplugging chuck 15c, which has a smaller teeth number to prevent dispersion of a chuck force and slippage of a plug, for a plastic material including resin.

EXPLANATIONS OF REFERENCE NUMERALS

1 Unplugging unit
2 Conveyor line
3 Sample rack entrance
4 Sample rack
5 Buffer
6 Sample rack identification section
7 Communication cable
8 unplugging position
9 Sample rack exit
10 Plug discard position
11 Plug detection sensor
12 Rack identification number
13a Rubber-plugged sample tube (press-in plug)
13b Resin-plugged sample tube (screw plug)
13c Resin-plugged sample tube (press-in plug)
13d, 13e Unplugged sample tube
14 Clamp device
15 Plug chuck device
15a unplugging chuck
15b Rubber-plug unplugging chuck suitable for rubber plug
15c Resin-plug unplugging chuck suitable for resin plug
16 Rubber plug
17 Resin plug
18 Screw
19a Teeth-shaped section of rubber-plug unplugging chuck
19b Teeth-shaped section of resin-plug unplugging chuck
20 Compression spring
21 Press section
22 Plugged sample tube
23 Plug of plugged sample tube
50 Controller

What is claimed is:

1. A system for pretreating a sample, comprising:
a conveyor line for conveying a sample rack on which at least one plugged sample tube is mounted; and
an unplugging unit for unplugging the plugged sample tube mounted on the sample rack conveyed by the conveyor line,
wherein the unplugging unit includes a clamp device for holding the plugged sample tube conveyed by the conveyor line at the time of unplugging; and a plug chuck device for chucking a plug of the plugged sample tube held by the clamp device and unplugging the plugged sample tube; and
the plug chuck device includes two types of unplugging chucks having plural protrusions at portions contacting the plug, and one of the two types of the unplugging chucks is disposed on top of the other.

2. The system for pretreating sample according to claim 1, wherein the number of the protrusions is different between the two types of the unplugging chucks in the plug chuck device.

3. The system for pretreating sample according to claim 1, wherein the number of the protrusions of an upper-side unplugging chuck of the two types of the unplugging chucks in the plug chuck device is larger than that of a lower-side unplugging chuck thereof.

4. The system for pretreating sample according to claim 1, wherein a relative position of the two types of the unplugging chucks in the plug chuck device is set adjustably in a direction of chucking the plug of the plugged sample tube.

5. The system for pretreating sample according to claim 1, wherein the plug chuck device unplugs the plugged sample tube by chucking the plug of the plugged sample tube and rotationally moving upward.

6. The system for pretreating sample according to claim 1, further comprising:
a controller for operating and controlling the system for pretreating sample; and
an identification section for reading an identification number assigned to the sample rack;
wherein the unplugging unit carries out unplugging operation on instructions of the controller based on the read identification number, depending on the plug of the plugged sample tube.

7. The system for pretreating sample according to claim 6, wherein the unplugging unit does not carry out the unplugging operation of the sample tube on the instructions of the controller based on the read identification number either when the sample tube does not require to be unplugged or when the sample tube does not have a plug.

8. The system for pretreating sample according to claim 6, further comprising:
an error sample storage;
wherein, when the unplugging operation is unsuccessful, the unplugging unit repeats the unplugging operation predetermined times, and, when all the unplugging operations of the predetermined times are unsuccessful, the unplugging unit conveys the sample rack to the error sample storage as a plugging error, the sample rack carrying the sample tube for which all the unplugging operations is unsuccessful.

9. The system for pretreating sample according to claim 2, wherein an unplugging chuck having more protrusions of the two types of the unplugging chucks is equipped to chuck a plug made of an elastic material, and another unplugging chuck having fewer protrusions of the two types of the unplugging chucks is equipped to chuck a plug made of a plastic material.

10. The system for pretreating sample according to claim 2, wherein the number of the protrusions of an upper-side unplugging chuck of the two types of the unplugging chucks in the plug chuck device is smaller than that of a lower-side unplugging chuck thereof.

11. The system for pretreating sample according to claim 1, wherein the plug chuck device includes a first type of unplugging chuck and a second type of unplugging chuck, and one of the two types of the unplugging chucks is disposed on top of the other.

* * * * *